(12) United States Patent
Liu

(10) Patent No.: US 7,388,656 B2
(45) Date of Patent: Jun. 17, 2008

(54) METHOD AND SYSTEM FOR COLOR GRADING OF GEMSTONES

(76) Inventor: Yan Liu, 1460 Rock Haven St., Monterey Park, CA (US) 91754

(*) Notice: Subject to any disclaimer, the term of this patent is extended or adjusted under 35 U.S.C. 154(b) by 188 days.

(21) Appl. No.: 11/322,431

(22) Filed: Dec. 30, 2005

(65) Prior Publication Data

US 2007/0153256 A1 Jul. 5, 2007

(51) Int. Cl.
*G01N 21/87* (2006.01)
(52) U.S. Cl. ...................................................... 356/30
(58) Field of Classification Search ................ 356/30; 358/521; 345/426
See application file for complete search history.

(56) References Cited

U.S. PATENT DOCUMENTS

| | | | |
|---|---|---|---|
| 1,617,024 | A | 2/1927 | Munsell |
| 4,056,952 | A | 11/1977 | Okuda |
| 4,508,449 | A | 4/1985 | Okazaki |
| 4,527,895 | A | 7/1985 | Rubin |
| 4,534,644 | A | 8/1985 | Beesley |
| 5,005,971 | A | 4/1991 | Davis |
| 5,143,212 | A | 9/1992 | Roberts |
| 5,615,005 | A * | 3/1997 | Valente et al. ............... 356/30 |
| 5,619,349 | A * | 4/1997 | Ueda et al. ................. 358/521 |
| 6,473,164 | B1 | 10/2002 | De Jong et al. |
| 6,853,387 | B2 | 2/2005 | Evanicky et al. |
| 6,980,283 | B1 * | 12/2005 | Aggarwal ..................... 356/30 |
| 2006/0001665 | A1 * | 1/2006 | Kupersmit ................... 345/426 |

OTHER PUBLICATIONS

Kelly et al, Color: Universal Language and Dictionary of Names, pp. i-34 pp. a1-a19, NBS Special Publication 440, U.S. Government Printing Office, Washington DC (1976). U.S.
King et al, Color Grading of Colored Diamonds in the GIA Gem Trade Laboratory, pp. 220-242, Gems & Gemology Magazine, vol. 30, No. 4, (Winter 1994). U.S.

* cited by examiner

*Primary Examiner*—F. L. Evans
*Assistant Examiner*—Abdullahi Nur
(74) *Attorney, Agent, or Firm*—Charles C. H. Wu; Wu & Cheung, LLP

(57) ABSTRACT

A method and system, including a computer program product, implementing a color terminology for accurate color grading of gemstones are provided. The method includes generating a reference color to match that of a graded gemstone under the standard viewing environment, processing color data in different color spaces, assigning a color grade to specify the color of the gemstone graded. The reference color can be continuously changed by adjusting the hue, lightness and saturation values. The color grade comprises a color name and one or more corresponding color coordinates and/or one or more corresponding color notations, in the form of Color Name (Color Coordinates). The color name is used for verbal description of the color, and the color coordinate or color notation is for accurate color communication in the jewelry industry.

20 Claims, 3 Drawing Sheets

|  | Fancy | Intense | Strong | Vivid |
|---|---|---|---|---|
|  | Fancy Brilliant | Intense Brilliant | Strong Brilliant | Vivid Brilliant |
| Brilliant |  |  |  |  |
|  | Fancy Light | Intense Light | Strong Light | Vivid Light |
| Light |  |  |  |  |
| Medium | Fancy Medium | Intense Medium | Strong Medium | Vivid Medium |
| Deep |  |  |  |  |
|  | Fancy Deep | Intense Deep | Strong Deep | Vivid Deep |
| Dark |  |  |  |  |
|  | Fancy Dark | Intense Dark | Strong Dark | Vivid Dark |

Fig. 3

METHOD AND SYSTEM FOR COLOR GRADING OF GEMSTONES

BACKGROUND OF THE INVENTION

1. Field of the Invention

The present invention relates in general to color grading of gemstones. More particularly, the present invention relates to a method and system, including a computer program product, for implementing a color terminology in color grading of gemstones.

2. Description of Related Art

Colors of gemstones are usually graded visually against discrete color samples. For example, U.S. Pat. No. 1,617,024 to Munsell describes color chips. U.S. Pat. No. 4,534,644 to Beesley describes simulating color standards. U.S. Pat. No. 4,527,895 to Rubin describes reference color charts. U.S. Pat. No. 5,005,971 to Davis describes resin color chips, and U.S. Pat. No. 5,143,212 to Roberts describes simulated gemstones.

In known gemstone color grading, the color of gemstones can only be approximately graded using the above-referenced patented methods and systems typically using discrete color samples. In practice, each color grade represents a large or very large volume in color space for the discrete color samples. Thus, such methods or systems for color grading of gemstones are not accurate because of the occupation of significantly large volume in color space for each color grade. For example, two gemstones with the same known color grade based upon know methods and systems may actually have a very large color difference. Therefore, the two gemstones may show totally different perceptual colors, such as a dark brown color and a red color.

Several devices were patented for measuring colors ranging from colorless to light yellow for diamonds (D-Z color scale). U.S. Pat. No. 4,056,952 to Okuda describes a colorimeter, and U.S. Pat. No. 4,508,449 to Okazaki describes a spectrophotometer. U.S. Pat. No. 6,473,164 to DeJong et al describes a color device assigned to the Gemological Institute of America (GIA).

Both the Okuda colorimeter and the Okazaki spectrophotometer use an integrating sphere to measure the color, but their accuracies are not high enough for color grading of colors ranging from colorless to light yellow in diamonds. The GIA color device simulates the condition of human visual color grading for colorless to light yellow diamonds, but the detector does not have the basic function of self-focus of the human eye. Further, the fluorescent daylight tube is not stable enough for color measurement. Thus devices such as the GIA color device are not accurate for the purpose of color grading for colorless to light yellow diamonds.

U.S. Pat. No. 5,615,005 to Valente et al describes an imaging device for evaluating gemstones. The evaluation includes color grading of gemstones. The Valente device utilizes a band pass filter and a detector array to obtain spectral photometric data for each individual pixel of a complete color image for evaluating gemstone. However, this device is not well accepted by the jewelry industry since it does not accurately grade the color of the gemstones. The band pass filter may not be very stable in general, and the device may not be well profiled for color processing and color display.

GIA produced a color image device called ColorMaster for color grading of gemstones. The ColorMaster has three primary R, G and B knobs for adjusting the color of a simulated gemstone image. Due to the ColorMaster's original design problems, it is not suitable for color grading of gemstones. For example, it may result in a significantly large color shift for each ColorMaster due to no user calibration, thereby resulting in large color differences among different ColorMasters. In addition, the GIA color description system is not well defined in color space, and is awkward for verbal communication purposes. The ColorMaster has been abandoned.

Recently, GIA has been utilizing a software named Gemewizard to assist students in the teaching of its Colored Stones courses using the GIA color description system for colored gemstones. The software displays each hue page with about 36 separated color images. However, the software can only display discrete color images. Further, each color grade represents a large volume of color space. Thus the true color of a gemstone cannot be graded by the Gemewizard software.

The International Color Consortium promotes standardizing color management by color profile. The color profile defines how color can be rendered accurately. Color profiles can be used to display accurate colors in computer monitors. U.S. Pat. No. 5,619,349 to Ueda et al describes a device for calibrating display color of a CRT to a color standard, and U.S. Pat. No. 6,853,387 to Evanicky et al describes a system for compact flat panel color calibration. Several commercial available devices can be used to calibrate color monitors for accurate color display.

In Kelly et al *Color: Universal Language and Dictionary of Names*, NBS Special Publication 440, U.S. Government Printing Office, Wash., D.C., (1976), a method of designating colors and defining color names in the Munsell color space is introduced. Color terminologies used for color grading of gemstones are usually concerned with the fineness of level 3 for color designation. The GIA colored diamond grading system (see King et al, Gem & Gemology, 1994) for example, has only nine color grades for each hue, and about half of the grades are concentrated in a very small volume in color space with low saturation and high lightness. Other color grades cover a very large area. Each color grade actually represents a very large range of colors. Thus, known color grading systems cannot accurately represent any individual color such as the color of a diamond.

Therefore, the need arises for a method and system to provide accurate reference color for color grading of gemstones, to process the color data, to designate a color grade comprising of color names for verbal description and color coordinate or color notations for accurate color communication in the jewelry industry.

SUMMARY OF THE INVENTION

In general, the present invention provides a method and system, including a computer program product, to accurately generate a reference color that can be adjusted continuously for color grading of gemstones. The system comprises of a color display element, a data processor, a computer program product, a CIE daylight simulator, and a neutral surrounding and background.

The present invention also provides a terminology for verbal color description of the color of gemstones. The color grade of this invention includes a color name for verbal color description and one or more color coordinates or color notations for accurate color communication.

The present invention provides a method, which comprises of display element calibration, color observation under standard viewing environment, color data processing, $\gamma$ correction, color name assignment, color display, decision making, and color grading report printing. The color grade of this invention is in the form of "Color Name (Color Coordinates)", which makes it possible for the color of a gemstone to be verbally described by a color name, and more importantly, numerically represented by one or more additional color coordinates or color notations for accurate color communication in the jewelry industry.

The present invention provides a computer program product, which can interface with an operator, usually a trained gemstone color grader in the jewelry industry or a jeweler, to adjust the hue, lightness and saturation values of the reference color on the display element to match the color of a gemstone being graded. The computer program product simultaneously calculates color data and provides a color name and a CIE 1976 (L*, a*, b*) (hereinafter CIELAB) coordinate, and other color coordinates and color notations.

The present invention can be used for color grading of any kinds of gemstones including colored diamonds. The color terminology of the present invention is also suitable for all kinds of gemstones. The computer program product can approximately convert the color terminology to the color terms of any other color description systems and color grading systems.

The present invention can also be used for color communication purpose by entering the color coordinates to display the corresponding color on the display element. The present invention solves the problem of inaccurate color description caused by verbal color description or by the discrete color grade obtained by other color grading methods and systems. Jewelers will always see the same true color on the display elements as long as they enter the same color coordinate of the color grade using the present invention.

A method for color grading of gemstones using a system with a computer program product is provided. The method includes: calibrating the display element to the specifications of the white point of a CIE standard illuminant, a certain brightness level with a γ correction; observing the average color of a gemstone under a standard viewing environment including 45/0 or 0/45 illuminating and viewing conditions, standard CIE D65 daylight simulator with a visible wavelength metamerism index MIvis B or better, illumination level at 1080 to 1340 1x and neutral background and surround with a Munsell notation N6 to N7; adjusting the hue, lightness and saturation values continuously to change the reference color by a color grader; calculating color coordinates and color notations from the hue, lightness and saturation values; applying γ correction to the RGB tristiumlus values; calculating the RGB digital counts; assigning a corresponding color name from the calculated color coordinates by checking the color name look-up table; displaying the color grade comprising a color name and one or more color coordinates and/or color notations; displaying the reference color on the display element; making a logical decision; if the reference color does not match the viewed average color of the gemstone, the computer program goes back to allow the color grader to match the viewed color again by readjusting the hue, lightness and saturation values; if the reference color matches the viewed color, the computer program instructs a printer to print out a color grade report for the gemstones with the color grade, including the color name, color coordinates and/or color notations obtained by using the present invention, and physical and gemological properties of the gemstone. The method also includes displaying the true color of a gemstone by inputting the color coordinate of its color grade for color communication purpose.

A computer program product stored on a machine-readable medium for processing color grading of gemstone is provided. The product comprises of instructions operable to cause a programmable data processor to: receive the inputted hue, lightness and saturation values; calculate color coordinates from the hue, lightness and saturation values for adjusting the reference color; apply γ correction to the RGB tristimulus values; calculate the RGB digital counts; assign a corresponding color name from the calculated color coordinates by checking the color name look-up table; instruct the data processor to drive the display element to show the reference color; instruct the printer to print out a color grading report with the color grade for the gemstone graded, including the color name, color coordinates, color notations, physical properties and gemological properties of the gemstone.

BRIEF DESCRIPTION OF THE DRAWING

FIG. 3 is a color name grid of the color terminology of the present invention.

DETAILED DESCRIPTION OF THE INVENTION

Figure 1:
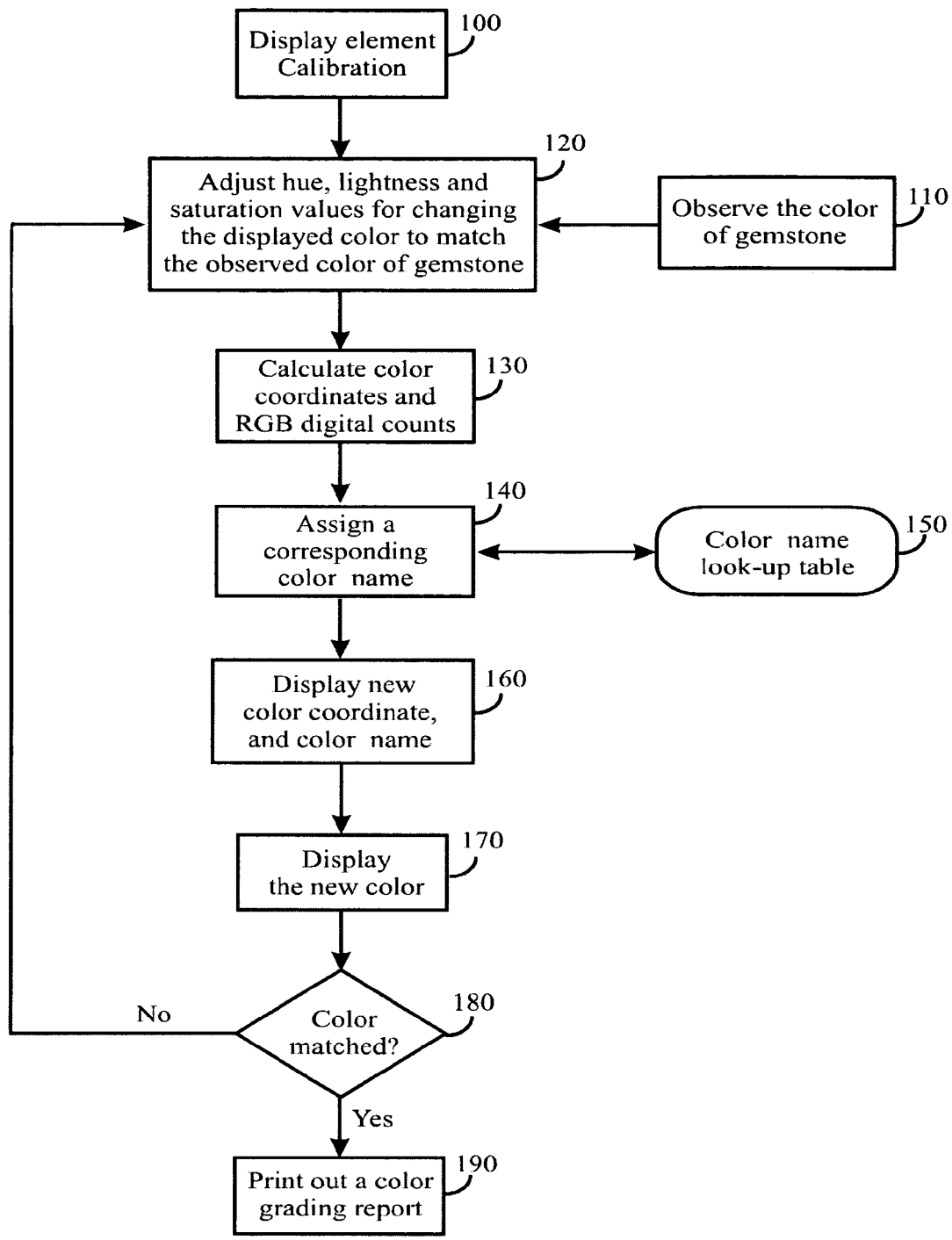
FIG. 1 is a flowchart of a gemstone color grading process in accordance with the present invention.

Referring to FIG. 1, a process of color grading of gemstones in accordance with the present invention is shown. The first step 100 of the process is display element calibration. The display element is calibrated to the specifications of the white point of one of the CIE standard illuminants at a specified brightness level, such as 160 nit. Usually the white point is the white point of CIE illuminant D65 that represents the average northern daylight. The RGB digital count response curves associated with the display element are corrected by the γ function. After the calibration a color profile file associated with the display element is generated. The color profile file is in turn stored in the data processor and used to define the characteristics of the display element for accurately displaying colors.

The color of a gemstone is visually observed under a daylight simulator with a color temperature of 6500 K 110. The color temperature of the daylight simulator is the same as that of the white point for calibrating the display element. The illuminating and viewing condition shall be the CIE standard with 45 degree illuminating and 0 degree viewing (45/0). Alternatively, the illuminating and viewing conditions may be 0 degree illuminating and 45 degree viewing (0/45). The illuminating level may be 1080 to 1340 1x at the center viewing area. It is noted that in viewing very dark gemstones, the illuminating level may be as high as 2150 1x. The surround and background may be the neutral color with the Munsell notation between N6 to N7.

Typically the color distribution in the face-up view of a faceted gemstone is not uniform. The average color shall be assigned to represent the color of the gemstone. When the gemstone is far from the color grader, its color may be blurred. The blurred color is defined as the average color. The average color may also be obtained by locating the color area in the face-up view that represents the color with average lightness and saturation. The 45/0 or the 0/45 illuminating and viewing conditions shall keep the directly reflected light from entering the eye of a human color grader.

However, under certain conditions, if the directly reflected light enters the eye, a small angle change within 5 degree can usually avoid this problem.

The reference color is changed by adjusting hue, lightness and saturation values. The adjustment is achieved by means of changing the values of the corresponding control scroll bars 120. Each time the value of a control scroll bar is changed, the computer program product calculates the new color coordinates and the new RGB digital counts 130 as well as assigns a new color name 140, 150. The display element displays the new color coordinates and new color name 160. The display element also simultaneously displays the new reference color 170.

The display element shows the reference color in a small area immediately surrounded by a large area of neural color with the Munsell color notation N6-N7 170. The color of the large surround area is the same as that of the surround and background for visual color observation 110. Both neutral colors may be Munsell color notation N6-N7. Since the reference color 170 and the viewed color 110 are against the same neutral background, the color comparison between them is not affected by different color contrasts.

Figure 2:
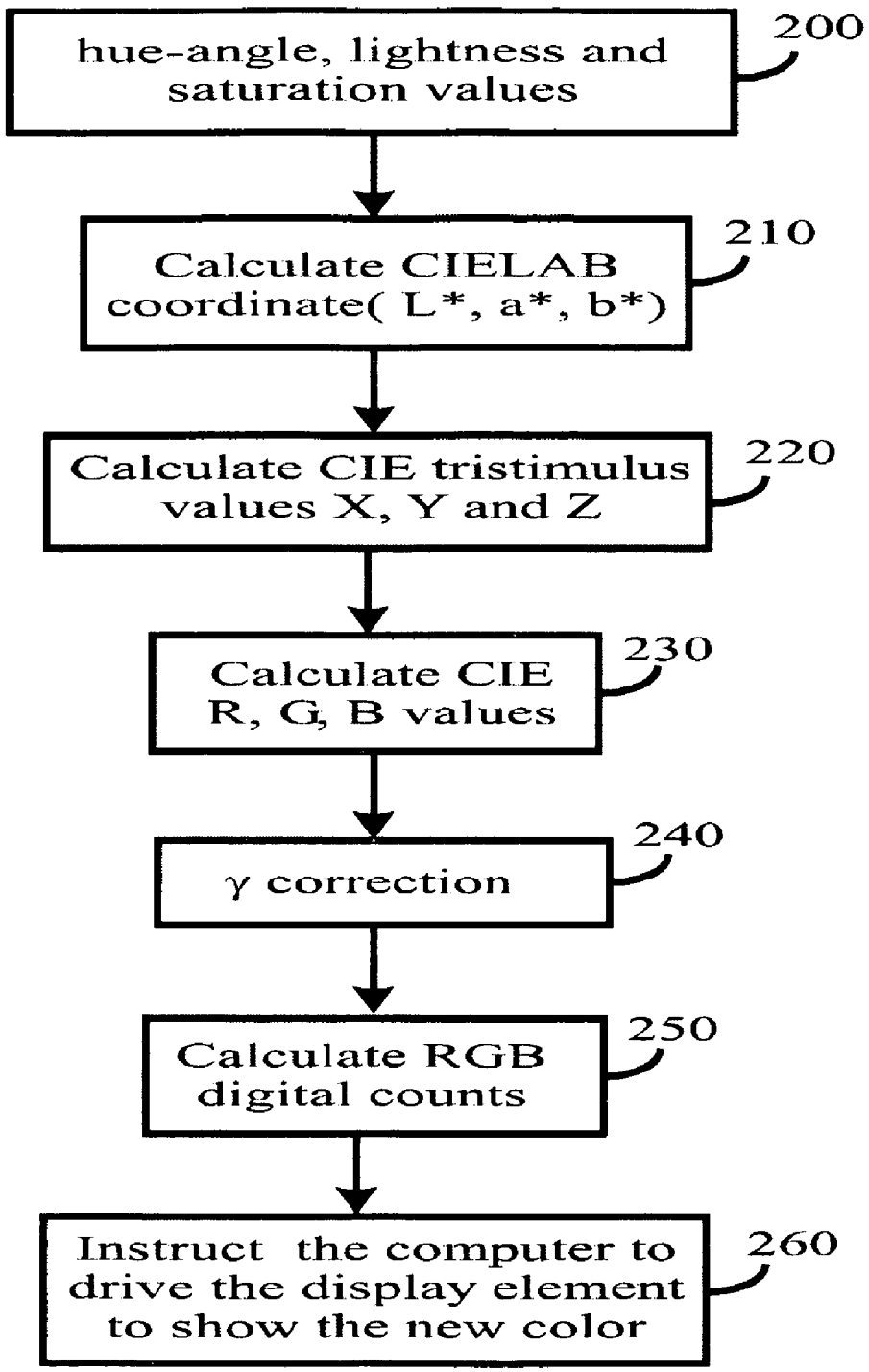
FIG. 2 is a flowchart of the computer program product of the present invention is shown.

Referring to FIG. 2, a detailed flowchart of the computer program product is depicted. The computer program product is used for calculating the color coordinates and the digital counts, assigning the color names, and instructing the data processor to drive the display element to show the reference color. More specifically, the computer program product calculates color coordinates and RGB digital counts 130. The computer program product uses the inputted hue, lightness and saturation values 200 to calculate the color coordinate ($L^*$, $a^*$, $b^*$) in the CIELAB color space 130. The CIE XYZ tristimulus values are then calculated from the CIELAB coordinate ($L^*$, $a^*$, $b^*$) 220. A transfer matrix is used to transfer CIE XYZ tristimulus values to CIE RGB tristimulus values 230. Since the response curves of a display element is nonlinear, the CIE RGB tristimulus values must be corrected by the $\gamma$ function 240. The value of $\gamma$ is typically 2.2 depending on the display element used. The $\gamma$ value here matches the $\gamma$ value used for the color calibration of the display element 100. The RGB digital counts are calculated from the $\gamma$ corrected RGB tristimulus values 250. The digital counts for black are zero, and that for white depends on the encoding for the RGB color channels. White digital counts of 255 may be for the 24-bit encoding (8-bit/channel). The $\gamma$ corrected digital counts 250 are sent to the display element by the data processor to display the reference color 260.

The computer program product checks the color name look-up table 150 to locate the corresponding color name for the calculated color coordinate ($L^*$, $a^*$, $b^*$) 140. The color name look-up table represents the relationship between the color names and the color coordinates in a specified color space, such as the CIELAB color space. Each color coordinate has a definite color name, but not vice versa, each color name covers a large volume of color space. Thus, the color coordinate can accurately represents the color of a gemstone, but the color name can only approximately represents the color. It is noted that the color coordinates are continues along their respective axles.

The color terminology of the present invention consists of hue terms, lightness levels and saturation intensities. The hue terms include primary colors, such as red, orange, yellow, green, blue, and violet, secondary colors, such as red orange, orange yellow, yellow green, green blue, and purple, as well as modified colors, such as purplish red, reddish orange, orangy red, yellowish orange, orangy yellow, greenish yellow, yellowish green, bluish green, greenish blue, and reddish purple. The lightness levels include white, brilliant, light, medium, deep, dark, and black. The white and black lightness levels only represent neutral colors within a very small saturation range (normally $C_{ab}^*<2.0$ in CIELAB color space) at very high lightness level or very low lightness level. The saturation intensities include fancy, intense, strong and vivid. The hue terms are usually arranged in a hue circle, and the lightness levels and saturation intensities are arranged in a lightness-saturation grid for each hue term as seen in FIG. 3. The saturation boundaries are at the highest intensity values of the corresponding saturations. The lightness boundaries of brilliant and light are at the lowest values of the corresponding lightness levels, the boundaries of deep and dark are at the highest values of the corresponding lightness levels, and lightness medium is between the boundaries of lightness light and lightness deep.

The color name in accordance with the color terminology of the present invention is written in the tripartite form of saturation, lightness and hue in this order to represent the reference color with the saturation intensity, lightness level, and hue-angle values 120. There are 4 saturation intensities, 7 lightness levels, and 22 hue names, with a total of 616 possible color names plus 7 neutral color names. Since the lightness white and black only exists for neutral colors and the high saturation intensities at high lightness and low lightness levels are limited, the actual number of the color names is about 380.

The color grade of a gemstone in accordance with the present invention comprises of a color name, and one or more color coordinates or color notations in the form:

Color Name (Color Coordinate 1) (Color Notation 1) . . .

where the color name is assigned by the computer program product in the tripartite form 140, and the coordinates and/or color notations are calculated in the steps 130, 210-250. The color coordinates can be in one or more color spaces, such as CIELAB, CIELUV and CIEXYZ color spaces, and the color notations may be in any of the Munsell, Natural Color and/or Pantone color spaces. The most common form of the color grade is "Color Name ($C_{ab}^*$, $L^*$, $h_{ab}$)", where $C_{ab}^*$ is the chroma, $L^*$ is lightness, and $h_{ab}$ is the hue-angle in the CIELAB color space. The chroma $C_{ab}^*$ represents saturation of a color in the CIELAB color space. Another common form of the color grade is "Color Name ($L^*$, $a^*$, $b^*$)". Further another common form of the color grade is "Color Name ($C_{ab}^*$, $L^*$, $h_{ab}$) ($L^*$, $a^*$, $b^*$)" in the CIELAB color space.

In fact, the higher the saturation is, the better the color is for the same lightness and hue name. Two rubies, for example, have the same lightness of 50 and same hue-angle of 27 degree and both are graded as vivid red, but the chroma (saturation) of one ruby is 60, and that of another ruby is 80. It is obvious that the color quality of the ruby with the chroma of 80 is much better than that of the ruby with the chroma of 60. The color grade in the form of Color Name ($C_{ab}^*$, $L^*$, $h_{ab}$) is very useful for directly indicating the color quality by the chroma $C_{ab}^*$, which represents saturation.

After calculating the color coordinates 130 and assigning the color name 140, the computer program product instructs the data processor to drive the display element to display the reference color 150. A color grader compares the reference color with the average color of the gemstone and makes a decision: Yes or No 180. If the decision is No, which means the reference color does not match the average color of the gemstone 110, the color grade readjusts hue, lightness and saturation values to match the average color of the gemstone again. The computer program goes back to input the readjusted hue-angle, lightness and saturation values 120, and goes through the steps 130 to 170 again, until the reference color matches the viewed average color of the gemstone graded.

If the viewed average color of a gemstone matches the reference color, the decision is Yes 180. The color name and the color coordinates of the displayed color are assigned as the color grade of the gemstone graded. The color of a ruby, for example, matches a reference color with a color name of Vivid Medium Red, a chroma value of 80.00, a lightness value of 50 and a hue value of 27.00. The color grade of the ruby is "Vivid Medium Red (80.00, 50.0, 27.00)." The color name "Vivid Medium Red" approximately represents the color of the ruby for verbal description in the gem trade. A jeweler can only know the approximate color of the ruby depending on the color name, and cannot know the true color. The color coordinate (CIELAB chroma, lightness and hue values) gives the true color of the ruby for communication purpose in the gem trade.

In the next step 190, the computer program product instructs a printer to print out a color grading report. The color grading report includes the color name, CIELAB coordinate (L*, a*, b*), hue-angle, lightness, and chroma values in CIELAB color space and other physical, gemological and colorimetric data. The color grading report can also be saved to a file such as a text file in the data processor.

This invention can also be used for color communication purpose among the jewelers at different places to see the same color if the jewelers use this invention. For example, if the color of a ruby is graded as "Vivid Medium Red (80.00, 50.0, 27.00)" by a jeweler or a gem laboratory using the present invention, the color grade of the ruby can be sent to jewelers anywhere in the world. The jewelers receiving the color grade can simply input the color coordinates into the system of this invention and the displayed color is exactly the same color of the ruby. As a benefit to the gem trade, this invention can be used for accurate color communication among jewelers and gem laboratories anywhere in the world.

It is important to note that while the present invention has been described in the context of a fully functioning data processing system, those of ordinary skill in the art will appreciate that the processes of the present invention is capable of being distributed in a form of a computer readable medium of instructions and in a variety of forms. Further, the present invention applies equally regardless of the particular type of signal bearing media that is used to carry out the distribution. Examples of computer readable media include recordable-type media such a floppy disc, a hard disk drive, a RAM, a CD-ROM, a DVD-ROM, flash memory chips, and transmission-type media such as digital and analog communications links, wired or wireless communications links using transmission forms such as, for example, radio frequency and light wave transmissions. The computer readable media may take the form coded formats that are decoded for actual use in a particular data processing system.

The present invention has been described in terms of particular embodiments. Other embodiments of the invention will appear to those skilled in the art from consideration of the specification and practice of the invention disclosed herein. For example, the color can be processed in different color spaces and still achieve desirable results. It is intended that the specification to be considered as exemplary only, with a true scope and spirit of the invention being indicated by the following claims.

What is claimed is:

1. A method for color grading of a gemstone using a system with a computer program product, comprising:
   calibrating a display element to a specification of a white point of a CIE standard illuminant at a brightness level with a γ correction;
   observing an average color of said gemstone by the 45/0 condition under a standard CIE daylight simulator against a neutral background and surround;
   adjusting a hue, a lightness and a saturation value continuously to change a reference color of the display element by a color grader;
   calculating a color coordinate and a color notation from said hue, said lightness and said saturation value;
   applying said γ correction to a RGB tristiumlus value;
   calculating a RGB digital counts;
   assigning a corresponding color name from said calculated color coordinates by checking a color name look-up table;
   making a logical decision;
   displaying said assigned color name and said calculated color coordinates; and
   displaying a reference color on said display element.

2. The method of claim 1 further comprising of printing a color grading report with a color grade for said gemstone graded, including said color name, said color coordinates said color notations, or a physical and a gemological property.

3. The method of claim 1 further comprising of displaying a true color of a gemstone by inputting said color coordinates of said color grade for a color communication purpose.

4. The method of claim 1, wherein
   said step of making a logical decision further comprising:
   allowing said color grader to match said reference color again by readjusting said hue, said lightness and said saturation value if said reference color does not match said viewed average color of the gemstone; or
   instructing a printer to print out a color grade report for the gemstone if the displayed color matches said viewed average color.

5. The method of claim 1, wherein said display element is a liquid crystal display (LCD), a cathode-ray tube (CRT), a plasma display, a digital light processing (DLP) display, or a liquid crystal on silicon (LCOS) display.

6. The method of claim 1, wherein said CIE standard illuminant is a CIE standard illuminant D50, a CIE standard illuminant D55, a CIE standard illuminant D65, a CIE standard illuminant D75, a CIE standard illuminant A, or a CIE standard illuminant C.

7. The method of claim 1, wherein a color space of said CIE standard illuminant is a CIE 1976 (L*, a* b*) color space, a CIE 1976 (L*, u*, v*) color space, a CIE 1931 (XYZ) color space, a CIE 1931 (RGB) color space, a CIE 1931 γ(RGB) color space, a CIE 1931 s(RGB) color space, a CIE 1964 (XYZ) color space, a CIE 1964 (RGB) color space, a CIE 1964 γ(RGB) color space, or a CIE 1964 s(RGB) color space.

8. The method of claim 1, wherein said standard CIE daylight simulator has a color temperature that is the same as that of a white point for calibrating the display element.

9. The method of claim 1, wherein the value said γ correction of the RGB tristimulus value is from 1.0 to 3.0 and a γ value for the display element calibration matches said γ correction of RGB tristimulus value.

10. The method of claim 1, wherein said reference color is immediately surrounded by a large area of neutral color with a Munsell notation N6-N7 and said reference color can be continuously adjusted by changing said hue, said lightness and said saturation value by changing a value of the a corresponding scroll bar.

11. The method of claim 1, wherein at least one interrelationship among said color names and said color coordinates is defined by said color name look-up table.

12. The method of claim 1, wherein said color name comprises of a saturation intensity, a lightness level, and a hue term in a tripartite form.

13. The method of claim 1, wherein said color grade of gemstone comprises of said color name and one or more color coordinates and one or more color notations in a form "Color Name ($C_{ab}^*$, $L^*$, $h_{ab}$)", in a form "Color Name ($L^*$, $a^*$, $b^*$)", in a form "Color Name ($C_{ab}^*$, $L^*$, $h_{ab}$) ($L^*$, $a^*$, $b^*$)", in a form "Color Name(H V/C)", in a form "Color Name(D C H)", or in a form "Color Name (Color Coordinate 1) (Color Notation 1)".

14. A computer program product stored on a machine-readable medium for processing color grading of a gemstone, the product comprises of instructions operable to cause a programmable data processor to:
    receive an input hue, an input lightness and an input saturation value;
    calculate a color coordinate from said input hue, said input lightness and said input saturation value for adjusting a reference color,
    apply a γ correction to RGB tristimulus values;
    calculate a RGB digital count;
    assign a corresponding color name from said calculated color coordinate by checking a color name lookup table; and
    instruct said programmable data processor to drive a display element to show said reference color.

15. The product of claim 14 further comprising of causing said programmable data processor to instruct a printer to print out a color grading report with a color grade for the gemstone graded including a color name, said color coordinate, a color notations, a physical property and a gemological property of said gemstone.

16. The product of claim 14, wherein said hue, said lightness and said saturation value can be continuously changed by adjusting a corresponding scroll bar, or by entering said color coordinate into a corresponding text box.

17. The product of claim 14, wherein the value of said γ correction to RGB tristimulus value is from 1.0 to 3.0 and a γ value for the display element calibration matches said γ correction of GRB tristimulus value.

18. The product of claim 14, wherein a color space of said CIE standard illuminant is a CIE 1976 ($L^*$, $a^*$ $b^*$) color space, a CIE 1976 ($L^*$, $u^*$, $v^*$) color space, a CIE 1931 (XYZ) color space, a CIE 1931 (RGB) color space, a CIE 1931 γ(RGB) color space, a CIE 1931 s(RGB) color space, a CIE 1964 (XYZ) color space, a CIE 1964 (RGB) color space, a CIE 1964 γ(RGB) color space, or a CIE 1964 s(RGB) color space.

19. The product of claim 15, wherein said RGB digital count is in a format of 12 bits color (4-bits for each color channel), 15 bits color (5-bits for each color channel), 16 bits color (4 bits for each color channel and additional 4 bits for a channel), 32-bits color (8 bits for each color channel and additional 8 bits), 64-bits color (16 bits for each color channel and additional 16 bits), 128-bits color (32 bits for each color channel and additional 32 bits), or 256-bits color (64 bits foe each color channel and addition 64 bits).

20. The method of claim 1, wherein the system comprises of said display element, a data processor instructed by said computer program product, said CIE standard illuminant D65 daylight simulator, and a neutral background that is surrounded with said Munsell notation N6-N7.

* * * * *